United States Patent
Xiao et al.

(10) Patent No.: US 10,857,385 B2
(45) Date of Patent: Dec. 8, 2020

(54) ADJUSTABLE COLLIMATOR, COLLIMATION SYSTEM, THERAPY HEAD AND RADIOTHERAPY DEVICE

(71) Applicants: OUR NEW MEDICAL TECHNOLOGIES, Shenzhen (CN); WUHAN CYBERMED SYSTEM CO., LTD., Wuhan (CN)

(72) Inventors: Shiqun Xiao, Shenzhen (CN); Haifeng Liu, Shenzhen (CN)

(73) Assignees: OUR NEW MEDICAL TECHNOLOGIES, Shenzhen (CN); WUHAN CYBERMED SYSTEM CO., LTD., Wuhan (CN)

(*) Notice: Subject to any disclaimer, the term of this patent is extended or adjusted under 35 U.S.C. 154(b) by 113 days.

(21) Appl. No.: 16/200,524

(22) Filed: Nov. 26, 2018

(65) Prior Publication Data
US 2019/0091489 A1    Mar. 28, 2019

Related U.S. Application Data

(63) Continuation of application No. PCT/CN2017/081654, filed on Apr. 24, 2017.

(30) Foreign Application Priority Data

May 26, 2016 (CN) .......................... 2016 1 0364879

(51) Int. Cl.
*A61N 5/10* (2006.01)
*G21K 1/04* (2006.01)

(52) U.S. Cl.
CPC ......... *A61N 5/1045* (2013.01); *A61N 5/1084* (2013.01); *G21K 1/046* (2013.01)

(58) Field of Classification Search
CPC ...... A61N 5/1045; A61N 5/1084; G21K 1/04; G21K 1/046
See application file for complete search history.

(56) References Cited

U.S. PATENT DOCUMENTS 6,044,126 A * 3/2000 Rousseau ............ A61N 5/1031
378/148
2005/0077459 A1 * 4/2005 Engler ................. A61N 5/1048
250/252.1

(Continued)

FOREIGN PATENT DOCUMENTS

CN       1530151 A    9/2004
CN     101151679 A    3/2008
(Continued)

*Primary Examiner* — Chih-Cheng Kao

(57) ABSTRACT

The present invention relates to the technical field of medical devices. Disclosed is an adjustable collimator, which can solve the problem that existing collimators cannot achieve precise therapy in a small irradiation field. The adjustable collimator comprises a controller and two blade sets arranged opposite to each other; the blade sets comprise a plurality of blades, the controller drives the blades to move so as to form a first irradiation field through which a ray can pass; at least one blade in the blade set is a small irradiation field blade, and at least one irradiation field hole is provided on the small irradiation field blade; the controller is further used to drive the small irradiation field blade to move such that the irradiation field hole becomes a second irradiation field through which the ray can pass, wherein the second irradiation field is smaller than the first irradiation field. The technical solutions of the present invention may achieve precise therapy on diseased parts, improving the therapeutic effect of radiotherapy.

10 Claims, 2 Drawing Sheets

(56) References Cited

U.S. PATENT DOCUMENTS

| | | | | |
|---|---|---|---|---|
| 2011/0013742 | A1* | 1/2011 | Zaiki | G21K 1/04 378/153 |
| 2017/0143995 | A1* | 5/2017 | Bergfjord | G21K 1/046 |

FOREIGN PATENT DOCUMENTS

| | | |
|---|---|---|
| CN | 203647890 U | 6/2014 |
| CN | 104338242 A | 2/2015 |
| CN | 105107093 A | 12/2015 |
| CN | 106075745 A | 11/2016 |
| EP | 0941540 B1 | 4/2003 |
| WO | 2012089535 A1 | 7/2012 |
| WO | 2015173327 A1 | 11/2015 |

\* cited by examiner

ADJUSTABLE COLLIMATOR, COLLIMATION SYSTEM, THERAPY HEAD AND RADIOTHERAPY DEVICE

TECHNICAL FIELD

The disclosure relates to the technical field of medical devices, in particular to an adjustable collimator, a collimation system, a therapy head and a radiotherapy device.

BACKGROUND

Existing radiotherapy devices usually adopt multi-source focusing to carry out radiotherapy on diseased parts, but due to the differences of the positions, sizes and therapy precision requirements of different diseased parts, different specifications of collimators need to be changed frequently for adjusting the diameter size and shape of a ray beam, and focusing target spots with different focusing sizes are formed so as to meet the shape, size and ray dosage required when a ray passes through the focusing target spots. However, due to the structural constraint of existing radiotherapy devices and collimators, the types of the existing collimators are few, the beam formed by the ray is single in shape and relatively large in irradiation field, but the precision requirement of small irradiation field therapy cannot be reached to cause that the precision of radiotherapy is relatively low to influence the therapy effect.

SUMMARY

In view of this, the present invention provides an adjustable collimator, a collimation system, a therapy head and a radiotherapy device, and solves the technical problem that existing collimators cannot achieve precise therapy in a small irradiation field so as to influence the therapeutic effect.

According to an embodiment of the present invention, the provided adjustable collimator comprises a controller and two blade sets arranged opposite to each other, the blade sets comprise a plurality of blades, the controller drives the blades to move so as to form a first irradiation field through which a ray can pass, at least one blade in the blade set is a small irradiation field blade, at least one irradiation field hole is provided on the small irradiation field blade, and the controller is further used to drive the small irradiation field blade to move such that the irradiation field hole becomes a second irradiation field through which the ray can pass.

For example, the small radiation field blade is provided at the central position of the blade set.

For example, the irradiation field holes on the small irradiation field blade are provided on the small irradiation field blade in an equally-spaced manner.

For example, the irradiation field holes on the small radiation field blade are different in hole diameters.

For example, the irradiation field holes on the small irradiation field blade are provided on the small irradiation field blade in size order.

For example, the irradiation field holes are provided from the center of the small irradiation field blade to two sides of the small irradiation field blade in size order sequentially.

For example, the controller comprises a first control module for controlling and driving the blades to move along the plane of a cutting ray so as to form the first irradiation field when an expected irradiation field is larger than or equal to the minimum value of the first irradiation field and a second control module for controlling and driving a second irradiation field hole with expected size in the small irradiation field blade so as to form the second irradiation field when the expected irradiation field is smaller than the minimum value of the first irradiation field.

For example, the widths of the small irradiation field blades are greater than those of other blades.

According to another embodiment of the present invention, a collimation system is provided, and the collimation system comprises a radioactive source and the adjustable collimator.

According to another embodiment of the present invention, a therapy head is provided, and the therapy head comprises at least two radioactive sources and any of the adjustable collimators provided in the embodiment of the present invention, and radioactive rays emitted by the radioactive sources are focused in the same area through the corresponding adjustable collimators.

According to another embodiment of the present invention, a radiotherapy device is provided, and the radiotherapy device comprises the adjustable collimator, the collimation system or the therapy head.

In the adjustable collimator, the collimation system, the therapy head and the radiotherapy device provided by the present invention, the adjustable collimator comprises a controller and two blade sets arranged opposite to each other, the blade sets comprise a plurality of blades, the controller drives the blades to move so as to form a first irradiation field through which a ray can pass, at least one blade in the blade set is a small irradiation field blade, at least one irradiation field hole is provided on the small irradiation field blade, and the controller is further used to drive the small irradiation field blade to move such that the irradiation field hole becomes a second irradiation field through which the ray can pass, so that the collimator provided in the embodiment of the present invention can quickly and flexibly form the first irradiation field or the second irradiation field according to the position, size and dosage requirements of an actual therapeutic ray so as to reach a conformal irradiation focus point with expected size and ray dosage, precise therapy on diseased parts is achieved, and the therapeutic effect of radiotherapy is improved.

BRIEF DESCRIPTION OF THE DRAWINGS

In order to illustrate the technical solutions in the embodiment of the present invention, the accompanying diagrams needing to be used in the embodiment are simply described. Apparently, the embodiments in the following description are merely a part rather than all of the embodiments of the disclosure. For ordinary technical staff in the art, under the premise of without contributing creative labor, other accompanying diagrams further can be obtained according to these accompanying diagrams.

DESCRIPTION OF THE EMBODIMENTS

The technical solutions of the present invention are further described in detail in conjunction with the following drawings and embodiments. Apparently, the embodiments in the following description are merely a part rather than all of the embodiments of the present invention. Based on the embodiment in the present invention, all other embodiments obtained by the ordinary technical staff in the art under the premise of without contributing creative labor belong to the scope protected by the present invention.

In the description of the present invention, it needs to be illustrated that the terms such as "first" and "second" are just used for description purpose, but cannot be understood to indicate or hint relative importance. In the description of the present invention, it further needs to be illustrated that, except as otherwise noted, the terms such as "link" and "connect" should be generally understood, for example, the components can be fixedly connected, and also can be detachably connected or integrally connected; the components can be mechanically connected, and also can be electrically connected; the components can be directly connected, also can be indirectly connected through an intermediate. For any person skilled in the art, the specific meanings of the terms in the present invention can be understood according to specific conditions. Moreover, in the description of the present invention, except as otherwise noted, the meaning of "a plurality of" indicates two or more than two.

Any process, method or block in the flowchart or described in other manners herein may be understood as being indicative of including one or more modules, segments or parts for realizing the codes of executable instructions of the steps in specific logic functions or processes, and that the scope of the preferred embodiments of the present invention include other implementations, wherein the functions may be executed in manners different from those shown or discussed (e.g., according to the related functions in a substantially simultaneous manner or in a reverse order), which shall be understood by a person skilled in the art.

Figure 1:
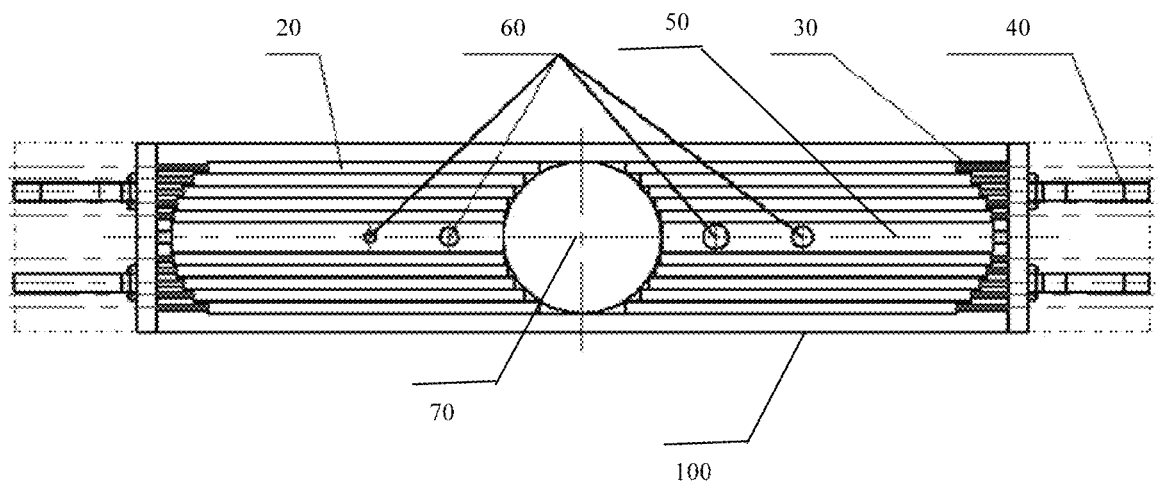
FIG. 1 is a structure diagram of an adjustable collimator in one embodiment of the present invention.

FIG. 1 is a structure diagram of an adjustable collimator 100 in one embodiment of the present invention. As shown in FIG. 1, the adjustable collimator 100 comprises two blade sets 20 arranged opposite to each other, a plurality of lead screws 30, a plurality of drive motors 40 and a controller (not shown). The blade sets 20 comprise a plurality of blades. The blades are correspondingly connected with the lead screws 30 and are oppositely arranged inside the inner accommodating space of the adjustable collimator 100. The drive motors 40 are connected with the lead screws 30, the controller is used for controlling the drive motors 40 to drive the lead screws 30 to drive the corresponding blades to move along the plane of the cutting ray so as to form a first irradiation field through which the ray can pass.

Wherein, the adjustable collimator 100 is of a regular cuboid structure internally provided with an accommodating space, and two sets of lead screws 30 are oppositely arranged at opposite positions inside the inner accommodating space of the inner side of the adjustable collimator 100. The lead screws 30 are cylinders arranged in parallel, the ends, close to the side wall of the adjustable collimator 100, of the lead screws 30 are connected with the drive motors 40 through connecting pieces, the ends, close to the center of the adjustable collimator 100, of the lead screws 30 are correspondingly connected with the end faces of the blades of the blade sets 20 in an adhesive bonding or buckle manner, and two sets of a plurality of oppositely arranged parallel line connecting bodies are formed inside the accommodating space of the adjustable collimator 100.

The two sets of drive motors 40 are arranged on the outer surface of the side wall of the adjustable collimator 100 in an equally-spaced manner. Each drive motor 40 is independently connected to one lead screw 30 through a connecting piece. Each of the drive motors 40 can be independently controlled by the controller arranged outside the side wall of the adjustable collimator 100 to drive the lead screws 30 to move along the plane of the cutting ray. The blades in the two blade sets 20 can be controlled to move according to a preset control command of the controller, and different sizes or shapes of first irradiation field holes 70 are formed together so as to adjust the position, size and ray dosage of the first irradiation fields, of the first irradiation field holes 70 in the middle of the two blade sets 20 inside the adjustable collimator 100, through which the ray can pass.

In this embodiment, for facilitating the position, size and ray dosage requirements of different rays during radiotherapy, the drive motors 40 can be controlled by the controller to drive the lead screws 30 and the blade sets 20 to move and adjust along the plane of the cutting ray. In this way, the first irradiation field hole 70 meeting the actual therapeutic ray can be formed, a conformal irradiation focus point with expected size and ray dosage can be formed when the ray passes through the first irradiation field holes 70, precise therapy on diseased parts is achieved, and the therapeutic effect of radiotherapy is improved.

Figure 2:
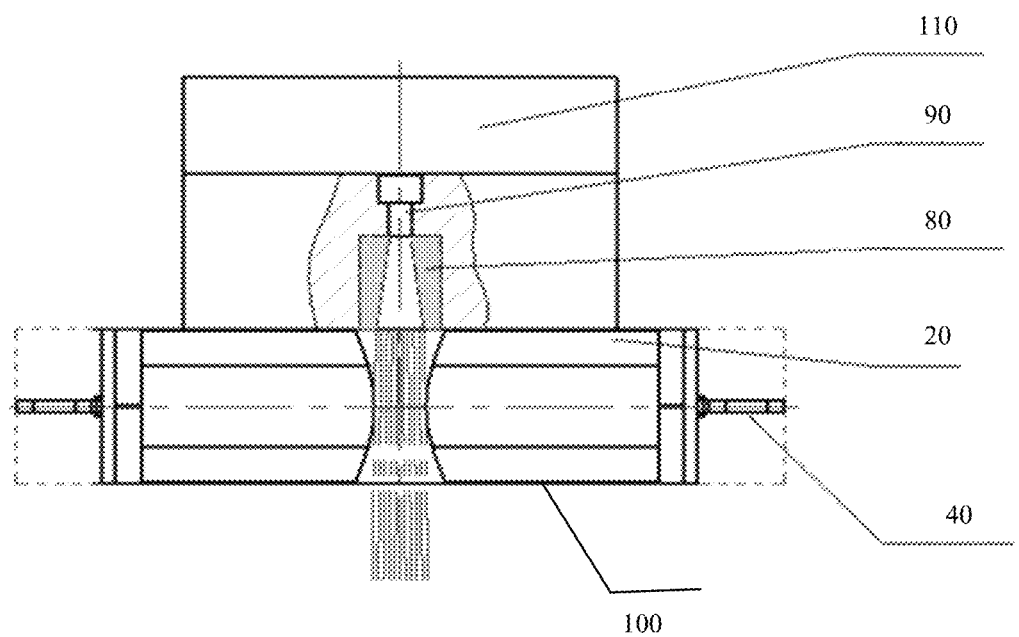
FIG. 2 is a structure diagram of the cross section of the adjustable collimator in one embodiment of the present invention.
Figure 3:
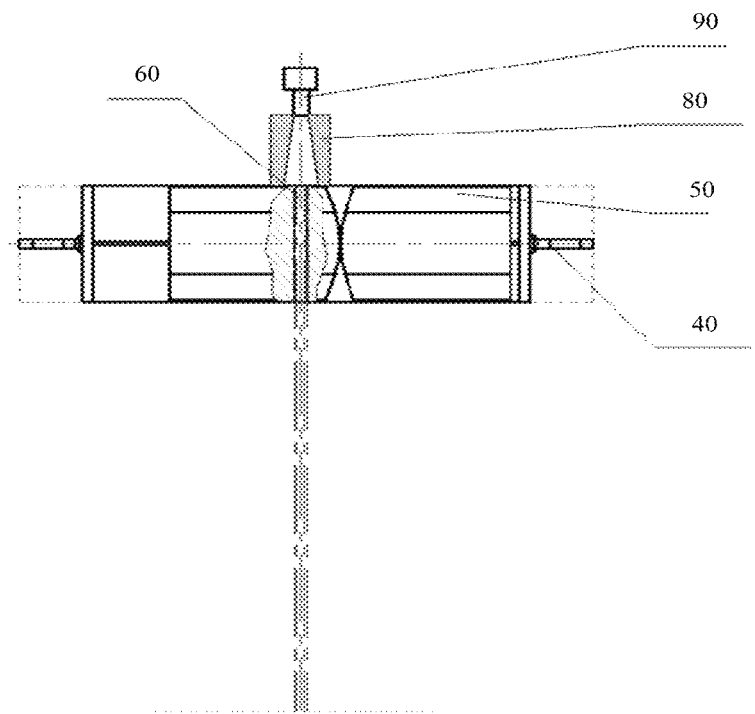
FIG. 3 is a structure diagram of the cross section of a collimation system in another embodiment of the present invention.

As shown in FIG. 1-FIG. 3, in this embodiment, in order to quickly adapt and adjust the size and ray dosage requirements of different rays, the two sets of opposite blades 50 at the central positions of the blade sets 20 are arranged to be small irradiation field blades. As an optimized embodiment, the widths of the small irradiation field blades 50 are greater than those of other blades. Further, the end faces, close to the center of the adjustable collimator 100, of the blades 50 are arranged in the shapes of circular arcs or polygons. For example, the irradiation field holes on the small radiation field blade may have different hole diameters. For example, as shown, at least one second irradiation field hole 60 with different sizes can be provided on the small irradiation field blade 50. The at least one second irradiation hole 60 can be arranged on the small irradiation field blade 50 in a size order or in an equally-spaced manner as shown. The second irradiation field holes 60 further can be arranged from the central position of the small irradiation field blade 50 to the two sides of the small irradiation field blade 50 in size order sequentially as also shown. The controller is further used for controlling the drive motors 40 to drive the second irradiation field hole 60 with expected size in the small irradiation field blade 50 to move below the ray so as to form the second irradiation field through which the ray can pass. The ray can pass through the second irradiation field hole 60 with expected size to form the conformal irradiation focus point with expected size and ray dosage, and precise therapy on diseased parts is achieved. The required second irradiation field holes 60 with different sizes can be flexibly arranged and selected in advance according to the requirements of actual radiotherapy, the size and ray dosage of the irradiation field target spot of the adjustable collimator 100 through which the ray can pass are quickly adjusted, precise therapy is achieved, and the work efficiency and therapeutic effect of radiotherapy are improved.

In this embodiment, the controller comprises a first control module and a second control module. Wherein, the first control module is used for controlling the blade sets 20 to move along the plane of the cutting ray so as to form the first irradiation field through which the ray can pass when the expected irradiation field is relatively large. The second control module for controlling the second irradiation field hole 60 with expected size in the small irradiation field blade 50 to move below the ray so as to form the second irradiation field when the expected irradiation field is relatively small. For facilitating the position, size and ray dosage requirements of different rays during radiotherapy, the blade sets 20 can be controlled by the first control module to move according to actual requirement so as to form the conformal irradiation focus point with expected size and ray dosage in the first irradiation field. When therapy needs a small irradiation field with specific or small size, the small irradiation hole 50 also can be controlled by the second control module to form the smaller irradiation field of the second irradiation field. In this way, the therapy irradiation focus point with expected ray dosage, high precision therapy is quickly realized, and the work efficiency and therapeutic effect of radiotherapy are improved.

It needs to be illustrated that, the first irradiation field is formed through the blades, particularly when the small irradiation field is formed, the half shadow of the ray is larger, through holes in the blades are in the second irradiation field, and the half shadow of the second irradiation field relative to the first irradiation field is smaller, so that when the small irradiation field is formed, therapy can be carried out by using the second irradiation field formed by the small irradiation field blades preferably, and the therapeutic effect is improved.

Shown in FIG. 3, is another embodiment of the present invention that provides a collimation system that includes a collimator illustrated in FIG. 2. It will be described with reference to FIG. 2. In some embodiments, the collimation system comprises a shielding body 110 (shown in FIG. 2), a radioactive source 90, a pre-collimator 80 and the adjustable collimator 100 in the embodiment. The radioactive source 90 is used for generating therapeutic rays such as gamma rays. The shielding body 110 (shown in FIG. 2) can be arranged on the outer side of the source body of the radioactive source 90, and can be used for sealing and shielding harmful ray radiation of the radioactive source 90. The pre-collimator 80 is arranged below a ray outlet of the radioactive source 90, and is used for preliminarily guiding the ray of the radioactive source 90 into the adjustable collimator 100. The adjustable collimator 100 is arranged below a ray outlet of the pre-collimator 80, the blade sets 20 are driven by the drive motors 40 to move along the plane of the cutting ray, and the position, size and ray dosage of the adjustable collimator 100 through which the ray passes can be quickly adjusted, so that precision therapy is quickly realized.

For example, the collimation system provided by the present invention comprises the radioactive source, the radioactive source also can be used for generating X rays, the collimation system can realize conformal irradiation radiotherapy through the adjustable collimator, and due to the fact that the adjustable collimator also comprises the small irradiation field blades, the second irradiation field also can be formed by using the small irradiation field blades, and more precision therapy is realized.

For example, the collimation system provided by the present invention comprises the radioactive source, the radioactive source can be used for generating X rays, the X rays can be divided into multiple beams through deflection, each beam is emitted through the corresponding adjustable collimator and focused in the same area, so that the collimation can be used for focusing therapy.

Figure 4:
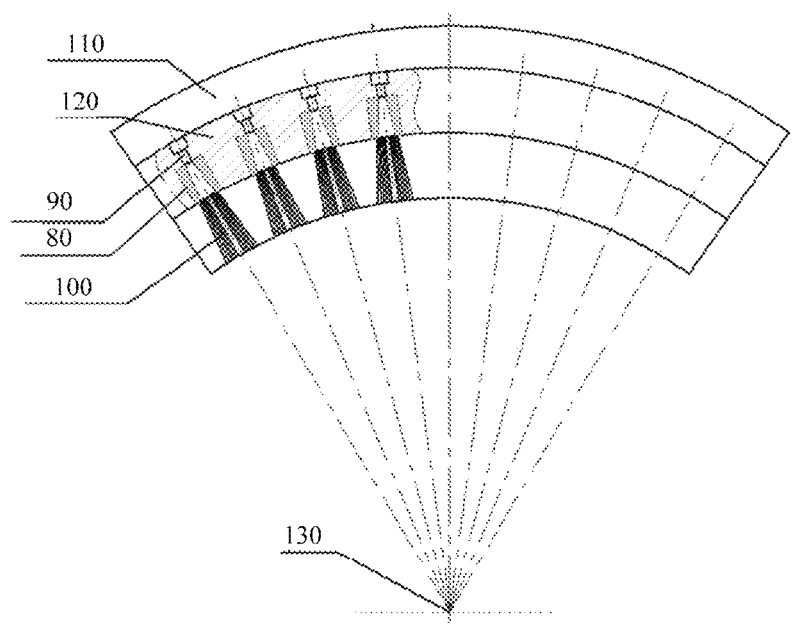
FIG. 4 is a structure diagram of the cross section of a therapy head in another embodiment of the present invention.

Shown in FIG. 4, based on the embodiment(s) described above, is another embodiment of the present invention that provides a therapy head, the therapy head comprises a shielding body 110, a source body 120, a plurality of pre-collimators 80 and a plurality of adjustable collimators 100 which are installed from outside to inside in sequence, the source body 120 is internally uniformly provided with a plurality of radioactive sources 90, the radioactive sources 90 are arranged above the ray inlets of the pre-collimators 80, the adjustable collimators 100 are arranged below the ray outlets of the pre-collimators 80, each radioactive source 90 is provided with the corresponding pre-collimator and the corresponding adjustable collimator 100 respectively, the radioactive rays emitted by the radioactive sources 90 can pass through the pre-collimators 80 and the adjustable collimators 100 to be focused in the same area 130, the therapy head can be used for quickly adjusting the position, size and ray dosage of the adjustable collimators 100 through which the ray can pass, and precision therapy is quickly realized. It needs to be illustrated that FIG. 4 is the therapy head as an example, it is understandable that the therapy head in the embodiment may comprise a plurality of radioactive sources and a plurality of adjustable collimators, and the pre-collimators can be arranged and also cannot be arranged between the radioactive sources and the adjustable collimators. The therapy head can be a therapy head for emitting gamma rays, also can be a linear accelerator therapy head for emitting X rays, or other types of therapy heads. Certainly, according to the difference of therapeutic purposes, the area 130 can be similar to tumor size and shape and also can be focus point, and the shape and size of the area 130 in the embodiment are not restricted specifically.

An embodiment of the present invention provides a radiotherapy device, the radiotherapy device comprises the adjustable collimator in the embodiment, the collimation system or the therapy head, and the position, size and ray dosage of the ray can be quickly adjusted by the radiotherapy device, so that precision therapy is quickly realized.

Above all, according to the adjustable collimator, the collimation system, the therapy head and the radiotherapy device provided by the present invention, the blade sets are controlled by the controller to move so as to form the first irradiation field, the second irradiation field is formed by controlling the movement of the second irradiation field hole in the small irradiation field blade, and the first irradiation field or the second irradiation field can be quickly and flexibly formed according to the position, size and ray dosage of the actual therapeutic ray so as to achieve the conformal irradiation focus point with expected size and ray dosage, so that precise therapy on diseased parts is achieved, and the therapeutic effect of radiotherapy is improved.

It should be understood that each component of the present invention can be realized by using hardware, software, firmware or the combination. In the embodiment, a plurality of steps or methods can be realized by using software or firmware which is stored in a storage device and is executed by an appropriate command executing system. For example, if the steps or methods are realized by using hardware, the steps or methods are the same in the another embodiment, and can be realized by using any one of the following technologies known in the field or the combination: a discrete logic circuit with a logic gate circuit for realizing a logic function for a data signal, a special integrated circuit with an appropriate combined logic gate circuit, a programmable gate array (PGA), a field-programmable gate array (FPGA) and the like.

In the description of the specification, the description of the reference terms such as "one embodiment", "some embodiments", "example", "specific example" or "some examples" indicates to be contained in at least one embodiment or example of the present invention in combination with specific characteristics, structures, materials or characteristics described by the embodiment or example. In the specification, the schematic expression for the above terms possibly indicates same embodiment or example. Moreover, the described specific features, structures, materials or characteristics can be combined in any of one or more embodiments or examples appropriately.

Although the embodiments of the present invention have already been illustrated and described, various changes, modifications, replacements and transformations can be made by any person skilled in the art under the condition of without departing from the spirit and the scope of the present invention, and thus the scope of the disclosure should be restricted by claims and equivalent scopes thereof.

What is claimed is:

1. A multi-leaf collimator comprising:
a controller and two leaf sets, the two leaf sets being arranged opposite to each other, wherein
each of the two leaf sets comprises a plurality of leaves, at least one leaf in the two leaf sets being a small irradiation field leaf, wherein at least one irradiation field hole is provided on the small irradiation field leaf; and
the controller driving the leaves of the two leaf sets is configured to:
move the leaves of the two leaf sets so as to form a first irradiation field through which a radioactive beam is permitted to pass, and
drive the small irradiation field leaf to move such that the irradiation field hole moves in a same direction as the small irradiation field leaf and forms a second irradiation field through which the radioactive beam is permitted to pass.

2. The multi-leaf collimator according to claim 1, where the small irradiation field leaf is provided at the central position of the leaf sets.

3. The multi-leaf collimator according to claim 1, wherein the at least one irradiation field hole includes more than one irradiation field hole that is provided on the small irradiation field leaf in an equally-spaced manner.

4. The multi-leaf collimator according to claim 1, wherein the at least one irradiation field hole includes more than one irradiation field hole that has different diameters.

5. The multi-leaf collimator according to claim 1, wherein the at least one irradiation field hole includes more than one irradiation field hole that is provided on the small irradiation field leaf in size order.

6. The multi-leaf collimator according to claim 1, wherein the at least one irradiation field hole includes more than one irradiation field hole that is provided from the center of the small irradiation field leaf to two sides of the small irradiation field leaf in size order sequentially.

7. The multi-leaf collimator according to claim 1, wherein the controller comprises a first control module for controlling and driving the leaves to move along a plane intersecting the radiation beam so as to form the first irradiation field when a desired irradiation field is larger than or equal to the minimum value of the first irradiation field and a second control module for controlling and driving a second irradiation field hole with a desired size in the small irradiation field leaf to move so as to form the second irradiation field when the desired irradiation field is smaller than the minimum value of the first irradiation field.

8. The multi-leaf collimator according to claim 1, wherein widths of the small irradiation field leaves are greater than those of other leaves.

9. A collimation system, comprising:
a radioactive source;
a pre-collimator; and
a multi-leaf collimator; and, wherein
the pre-collimator is arranged below the radioactive source and is configured to guide a radioactive beam emitted by the radioactive source into the multi-leaf collimator; and
the multi-leaf collimator is arranged below the pre-collimator and comprises a controller and two leaf sets, the two leaf sets being arranged opposite to each other, wherein
each of the leaf sets comprises a plurality of leaves, at least one leaf in the two leaf sets being a small irradiation field leaf, wherein at least one irradiation field hole is provided on the small irradiation field leaf; and
the controller driving the leaves of the two leaf sets is configured to:
move the leaves of the two leaf sets so as to form a first irradiation field through which the radioactive beam is permitted to pass, and
drive the small irradiation field leaf to move such that the irradiation field hole moves in a same direction as the small irradiation field leaf and forms a second irradiation field through which the radioactive beam is permitted to pass.

10. A therapy head, wherein the therapy head comprises;
a source body provided with a plurality of radioactive sources;
a plurality of pre-collimators; and
a plurality of multi-leaf collimators; and, wherein
the plurality of the radioactive sources are arranged below the plurality of the pre-collimators, wherein each of the plurality of the radioactive sources is provided with a corresponding one of the plurality of the pre-collimators and a corresponding one of the plurality of the multi-leaf collimators, and wherein radioactive beams emitted by the plurality of the radioactive sources are focused in a same area through the corresponding pre-collimators and multi-leaf collimators; and,
a given one of the multi-leaf collimators comprises a controller and two leaf sets, the two leaf sets being arranged opposite to each other, wherein
each of the leaf sets comprises a plurality of leaves, at least one leaf in the two leaf sets being a small irradiation field leaf, wherein at least one irradiation field hole is provided on the small irradiation field leaf; and
the controller driving the leaves of the two leaf sets is configured to:
move the leaves of the two leaf sets so as to form a first irradiation field through which a radioactive beam emitted by the radioactive source corresponding to the multi-leaf collimator is permitted to pass, and
drive the small irradiation field leaf to move such that the irradiation field hole moves in a same direction as the small irradiation field leaf and forms a second irradiation field through which the radioactive beam emitted by the radioactive source corresponding to the multi-leaf collimator is permitted to pass.

* * * * *